(12) United States Patent
McKenna

(10) Patent No.: US 7,180,978 B2
(45) Date of Patent: Feb. 20, 2007

(54) MAMMOGRAPHY UNIT POSITIONING SYSTEM AND METHOD

(75) Inventor: Gilbert McKenna, Revere, MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 10/888,300

(22) Filed: Jul. 9, 2004

(65) Prior Publication Data

US 2005/0100129 A1    May 12, 2005

Related U.S. Application Data

(60) Provisional application No. 60/485,840, filed on Jul. 9, 2003.

(51) Int. Cl.
*A61B 6/04* (2006.01)
(52) U.S. Cl. ....................................... 378/37
(58) Field of Classification Search .................... 378/37
See application file for complete search history.

(56) References Cited

U.S. PATENT DOCUMENTS

| 3,824,397 | A | | 7/1974 | Bauer et al. | |
|---|---|---|---|---|---|
| 4,203,037 | A | * | 5/1980 | Gur et al. | 378/37 |
| D315,207 | S | | 3/1991 | Korvenmaa | |
| 5,170,419 | A | * | 12/1992 | Johansson et al. | 378/37 |
| 5,305,365 | A | | 4/1994 | Coe | |
| 5,386,447 | A | * | 1/1995 | Siczek | 378/37 |
| 6,375,352 | B1 | * | 4/2002 | Hewes et al. | 378/196 |
| 2003/0194051 | A1 | * | 10/2003 | Wang et al. | 378/37 |

FOREIGN PATENT DOCUMENTS

JP        06285051 A  * 10/1994

* cited by examiner

*Primary Examiner*—Edward J. Glick
*Assistant Examiner*—Chih-Cheng Glen Kao
(74) *Attorney, Agent, or Firm*—McDermott Will & Emery LLP

(57) ABSTRACT

A system for positioning a mammography unit includes a C-arm, an x-ray tube mounted at one end of the C-arm, and a compressor-Bucky assembly mounted at an opposite end of the C-arm. The compressor-Bucky assembly includes a film receptor (preferably a Bucky grid) and a plate-like compressor. The x-ray tube and the compressor-Bucky assembly can be rotated together with the C-arm about a center of rotation. In addition, the x-ray tube and the compressor-Bucky assembly can be rotated independently of one another within the C-arm.

13 Claims, 7 Drawing Sheets

MAMMOGRAPHY UNIT POSITIONING SYSTEM AND METHOD

CROSS-REFERENCE TO RELATED APPLICATIONS

The present application claims priority to co-pending provisional U.S. patent application Ser. No. 60/485,840, which was filed on Jul. 9, 2003, is assigned to the assignee of the present application, and is incorporated herein by reference.

FIELD OF THE DISCLOSURE

The present disclosure relates generally to X-ray systems and, more particularly, to a system and method for supporting and positioning a mammography unit, including an X-ray tube and a film receptor, with respect to a patient for a mammography examination.

BACKGROUND OF THE DISCLOSURE

Mammography is a specific type of imaging that uses a low-dose x-ray system and high-contrast, high-resolution film for examination of the breasts. Most medical experts agree that successful treatment of breast cancer often is linked to early diagnosis. Mammography plays a central part in early detection of breast cancers because it can show changes in the breast up to two years before a patient or physician can feel them. Current guidelines from the U.S. Department of Health and Human Services (HHS), the American Cancer Society (ACS), the American Medical Association (AMA) and the American College of Radiology (ACR) recommend screening mammography every one to two years for women, beginning at age 40.

X-ray photography of the female breast constitutes one branch of the broader field relating to diagnostic X-ray photography of soft tissues, but the preparation of X-ray pictures of the female breast is very difficult, particularly in that the correct adjustment and focusing of the system is rather complicated. In the prior art, it was the general practice to prepare mammograms by utilizing the available standard X-ray installations, while equipping such installations with auxiliary devices. While it was possible to obtain satisfactory results in this way, there were various drawbacks and disadvantages. For example, the female patient rarely remained in the desired standard position during the preparation of the mammogram. Moreover, the problems of focusing and adjustment were so difficult that the quality of the results was variable and rather unpredictable.

Thus, the desire arose to provide a special X-ray machine which would satisfy the demands of the physicians for easy and accurate focusing and adjustment of the machine during X-ray photography of the female breast. U.S. Pat. No. 5,305,365 (the "'365 patent"), for example, discloses such a machine and is entitled "Mammography System With Rearwardly Tilting Mammograph". The '365 patent is directed to a mammography system that includes a variable angle, rearwardly tilting mammograph. The '365 patent discloses a mammograph that consists of an x-ray tube mounted at an upper end of a system arm, and a film receptor mounted opposite the x-ray tube at a lower end of the system arm. The '365 patent discloses that the mammograph is tiltably-rotate—mounted on a support structure. The '365 patent states that the tilting direction is rearward from the vertical, and that the tilting axis is horizontal, in front of the patient, and extending laterally from one side to the other of the patient. The system arm of the mammograph can also be rotated in addition to being tilted.

U.S. Pat. No. 3,824,397 is entitled "Device for X-Ray Photography, In Particular for Mammography" shows a device including a support which is connected to a telescopic horizontal arm, is rotatable about the axis of the arm, and is also tiltable about an axis which is perpendicular to the arm. U.S. Pat. No. Des. 315,207 is entitled "Mammography Unit" and shows a mammography unit which appears to be vertically movable on a support column.

What is still desired, however, is a new and improved system and method for positioning a mammography unit. Preferably, the new and improved system and method will allow the mammography unit to be vertically raised and lowered, rotated, and tilted. In addition, the new and improved system and method will preferably allow an X-ray tube and a film receptor of the mammography unit to be independently rotated.

SUMMARY OF THE DISCLOSURE

Exemplary embodiments of the present disclosure provide a new and improved system and method for positioning a mammography unit. A system constructed in accordance with the present disclosure can be used for, but is not limited to, positioning an X-ray tube and a film receptor of a mammography unit with respect to a patient's breast during a mammography examination procedure.

The system includes a C-arm, an x-ray tube mounted at one end of the C-arm, and a compressor-Bucky assembly mounted at an opposite end of the C-arm. The compressor-Bucky assembly includes a film receptor (preferably a Bucky grid) and a plate-like compressor. The x-ray tube and the compressor-Bucky assembly can be rotated together with the C-arm about a center of rotation. In addition, the x-ray tube and the compressor-Bucky assembly can be rotated independently of one another within the C-arm.

Among other features and advantages, the new and improved system and method of the present disclosure allows a mammography unit to be vertically raised and lowered, rotated, and tilted in preparation for a mammography examination. In addition, the new and improved system and method allows an X-ray tube and a film receptor of the mammography unit to be independently rotated, so that the X-ray tube and the film receptor can be even more precisely positioned with respect to a patient during a mammography examination. By enabling independent rotation of the x-ray tube and the compressor-Bucky assembly, the system provides increased comfort to the patient, and allows more breast tissue to be examined in a manner less stressful to the patient.

The foregoing and other features and advantages of the present disclosures will become more readily apparent from the following detailed description of the disclosure, as illustrated in the accompanying drawing.

BRIEF DESCRIPTION OF THE DRAWINGS

Like reference characters designate identical or corresponding components and units throughout the several views.

DETAILED DESCRIPTION OF EXEMPLARY EMBODIMENTS

Figure 1:
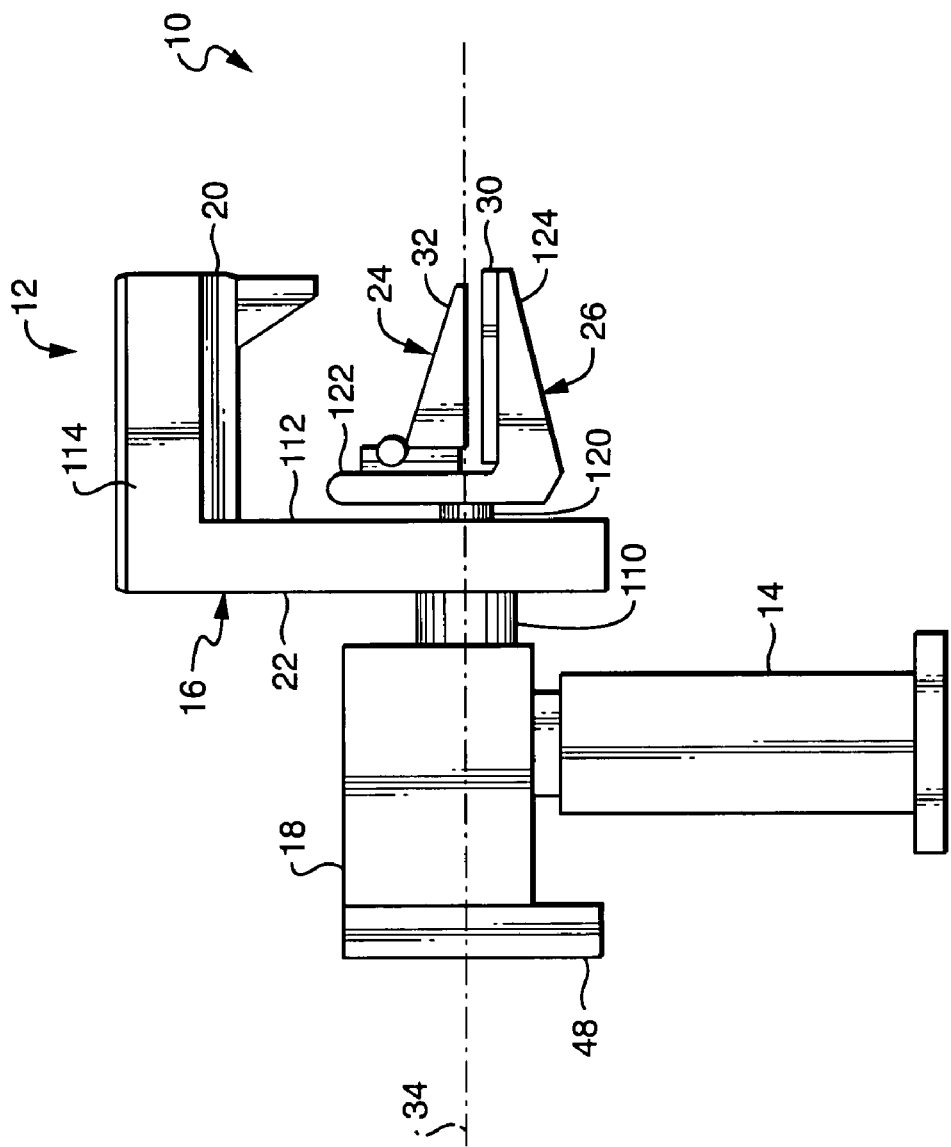
FIG. 1 is a side elevation view of an exemplary embodiment of a system constructed in accordance with the present disclosure including a mammography unit mounted on a telescoping vertical column, and wherein the column is shown in a fully lowered position.

Referring to FIGS. 1 through 4, an exemplary embodiment of an x-ray mammography system 10 constructed in accordance with the present disclosure is shown. The x-ray mammography system 10 includes a mammography unit 12 supported on a vertical support stand 14. The mammography unit 12 includes a C-arm 16 connected to the support stand 14 via a casement 18, an x-ray tube 20 mounted on a first portion 22 of the C-arm 16, and a compressor-Bucky assembly 24 mounted on a second portion 26 of the C-arm 16 so that it is opposite the x-ray tube 20.

The compressor-Bucky assembly 24 includes a film receptor 30 (preferably a Bucky grid) and a plate-like compressor 32. The compressor 32 is movable with respect to the film receptor 30 such that a woman's breast may be positioned and compressed between the compressor 32 and the film receptor 30 during a mammography examination.

Figure 3:
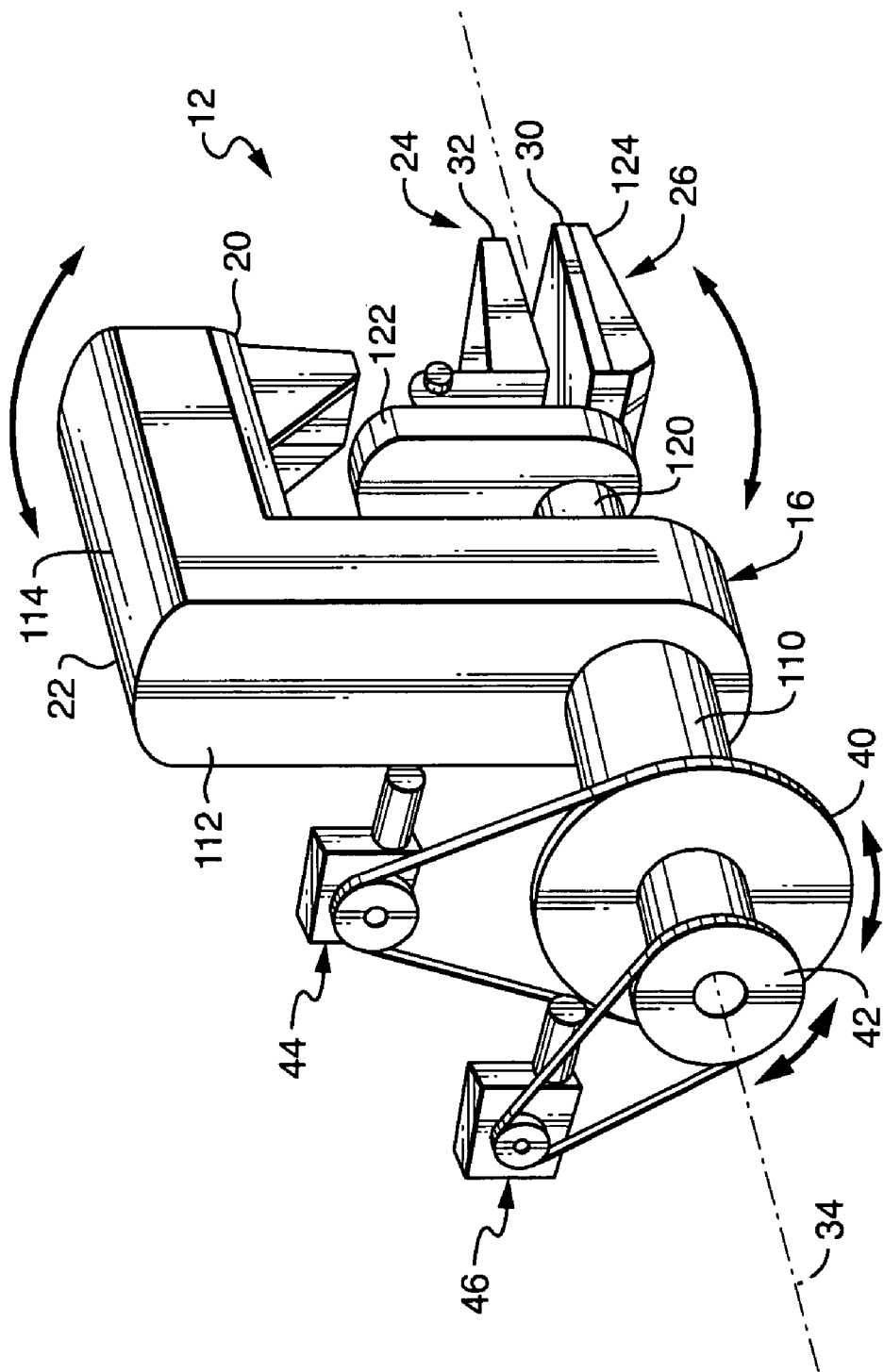
FIG. 3 is a top and end perspective view of the mammography unit of the system of FIG. 1.
Figure 4:
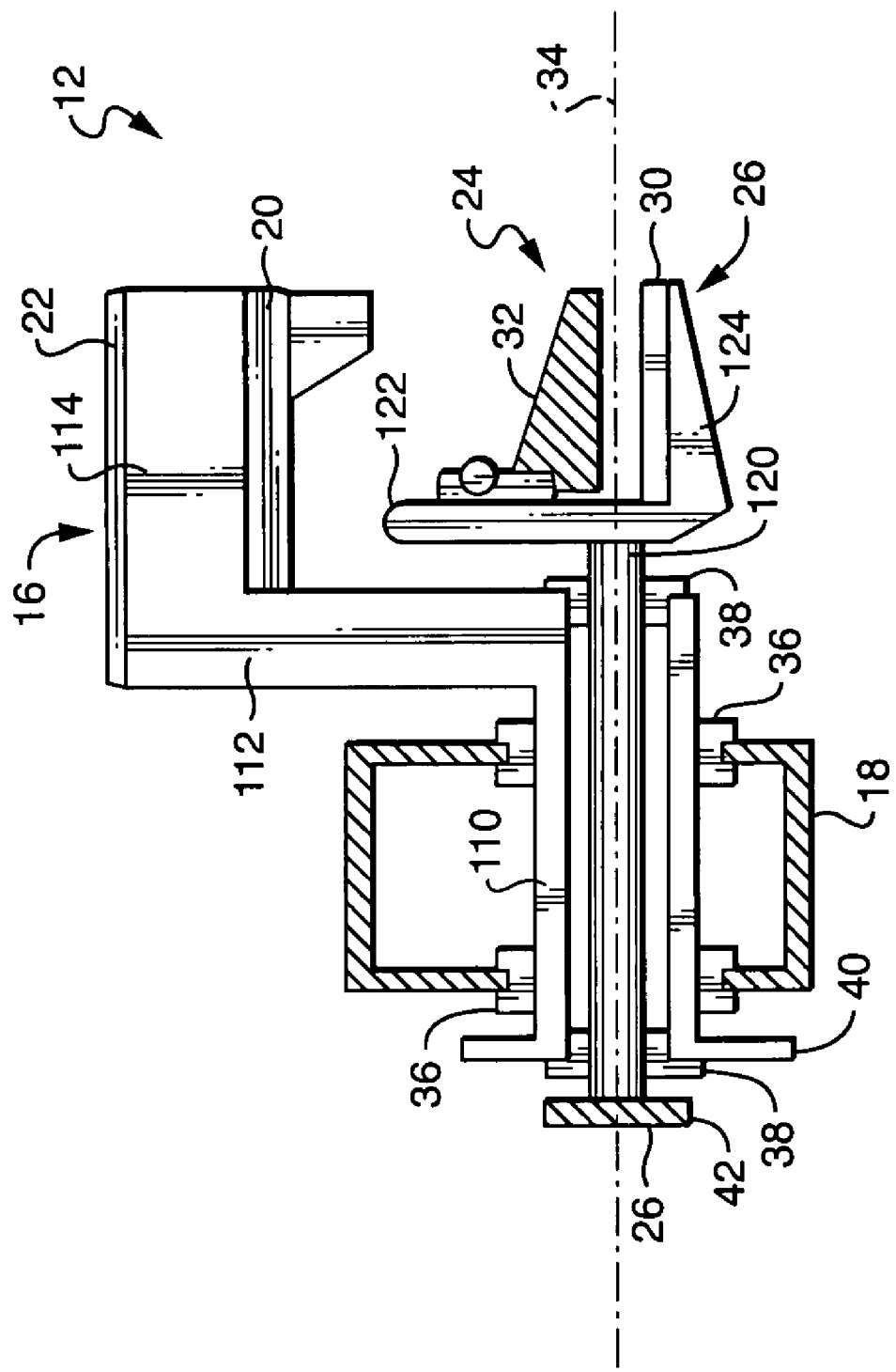
FIG. 4 is a side elevation view, partially in section, of the mammography unit of the system of FIG. 1.

The first and the second portions 22, 26 of the C-arm 16 are arranged so that the x-ray tube 20 and the compressor-Bucky assembly 24 can be rotated together with both portions 22, 26 of the C-arm 16 about a rotation axis 34, shown in FIGS. 1, 3 and 4. In addition, the x-ray tube 20 and the first portion 22 of the C-arm 16 can be rotated independently of the compressor-Bucky assembly 24 and the second portion 26 of the C-arm 16.

By enabling independent rotation of the x-ray tube 20 and the compressor-Bucky assembly 24, the system 10 improves the positioning of the patient during the initial clamping of a patient's breast, and then allows the x-ray tube to be moved with respect to the clamped breast. Independent rotation of the x-ray tube 20 and the compressor-Bucky assembly 24 provides increased comfort to the patient, and allows more breast tissue to be examined in a manner less stressful to the patient. For example, during the positioning of a patient for a vertical or overhead breast shot, the patient's face may interfere with or come in contact with the upper section of the C-arm 16 that houses the x-ray tube 20. It may be much easier and safer to rotate the C-arm 16 only, to the left or right, out of the patient's face and then position the breast to be imaged in the compressor-Bucky assembly 24. With the x-ray tube 20 out of the way, the patient is more comfortable and the x-ray tube 20 can be rotated back to the vertical position just before the actual x-ray image is taken.

Furthermore, independent rotation of the x-ray tube 20 and the compressor-Bucky assembly 24 supports stereotaxis imaging by allowing a breast to be held in a stationary position in the compressor-Bucky assembly 24 while the C-arm 16 is moved to the left or right and the breast is viewed from different angles. Stereotaxis imaging is especially useful for looking under a lesion or anomaly to see if the object is just one or actually multiple objects one on top of another. Stereotaxis images are also used for guiding Biopsy needles since imaging from different angles provides height information necessary to allow a sample to be taken.

In addition, independent rotation of the x-ray tube 20 and the compressor-Bucky assembly 24 improves tomography imaging by allowing additional volumetric information to be gained in the vertical plane about any anomaly or area of interest within a breast. Additional volumetric information is accomplished by holding the breast in the compressor-Bucky assembly 24 at a fixed position and then rotating the C-arm 16 and the x-ray tube 20 from −30 degrees to +30 degrees while taking multiple x-ray images during rotation of the C-arm. The information contained in the images can then be reconstructed in a variety of ways to produce additional depth-specific information about an image in the horizontal plane.

As shown best in FIG. 4, the first portion 22 of the C-arm 16 is mounted on a first set of bearings 36 in the casement 18 so that the first portion 22 of the C-arm 16 can rotate about the rotation axis 34. The first portion 22 of the C-arm 16 includes a base 110 that extends coaxially with the rotation axis 34, a proximal segment 112 connected to the base 110, and a distal segment 114 extending from the proximal segment 112. In the exemplary embodiment shown, the proximal segment 112 extends radially outwardly from the base 110 and perpendicular to the rotation axis 34, and the distal segment 114 extends parallel to the rotation axis 34. The x-ray tube 20 is mounted on the distal segment 114.

The second portion 26 of the C-arm 16 is coaxially mounted on a second set of bearings 38 in the casement 18 so that the second portion 26 of the C-arm 16 can also rotate about the rotation axis 34. The second portion 26 of the C-arm 16 is able to rotate about the rotation axis 34 independently of the first portion 22 of the C-arm 16. The second portion 26 of the C-arm 16 includes a base 120 that extends coaxially with the rotation axis 34, a proximal segment 122 connected to the base 120, and a distal segment 124 extending from the proximal segment 122. In the exemplary embodiment shown, the proximal segment 122 extends perpendicular to the rotation axis 34, and the distal segment 124 extends parallel to the rotation axis 34. The compressor 32 of the compressor-Bucky assembly 24 is mounted on the proximal segment 122 of the second portion 26, and the film receptor 30 is mounted on the distal segment 124.

In the exemplary embodiment shown, the base 110 of the first portion 22 of the C-arm 16 is tubular and the base 120 of the second portion 26 of the C-arm 16 is coaxially positioned within the base 110 of the first portion 22, and the second set of bearings 38 are positioned between the base 120 of the second portion 26 and the base 110 of the first portion 22. Alternatively, the C-arm 16 can be adapted and arranged so that the base 110 of the first portion 22 of the C-arm 16 is coaxially positioned within the base 120 of the second portion 26 of the C-arm 16.

The first portion 22 of the C-arm 16 includes a driven gear 40 secured to the base 110 and radially extending with respect to the rotation axis 34, and the second portion 26 of the C-arm 16 also includes a driven gear 42 secured to the base 120 and radially extending with respect to the rotation axis 34. As shown best in FIG. 3, the system 10 also includes a first drive assembly 44 operatively connected to the gear 40 of the first portion 22 of the C-arm 16 for rotating the first portion 22 of the C-arm 16 about the rotation axis 34, independently of the second portion 26 of the C-arm 16, and a second drive assembly 46 operatively connected to the gear 42 of the second portion 26 of the C-arm 16 for rotating the second portion 26 of the C-arm 16 about the rotation axis 34, independently of the first portion 22 of the C-arm 16. In the exemplary embodiment shown, the drive assemblies 44, 46 include motors having drive gears and pulleys operatively connecting the drive gears of the motors to the driven gears 40, 42 of the C-arm 16. The x-ray tube 20 and the compressor/Bucky assembly 24 can be rotated together or independently, as needed, providing increased flexibility in the use of the system 10. The drive assemblies 44, 46 are normally contained in a cover 48, which is shown in FIG. 1.

Figure 2:
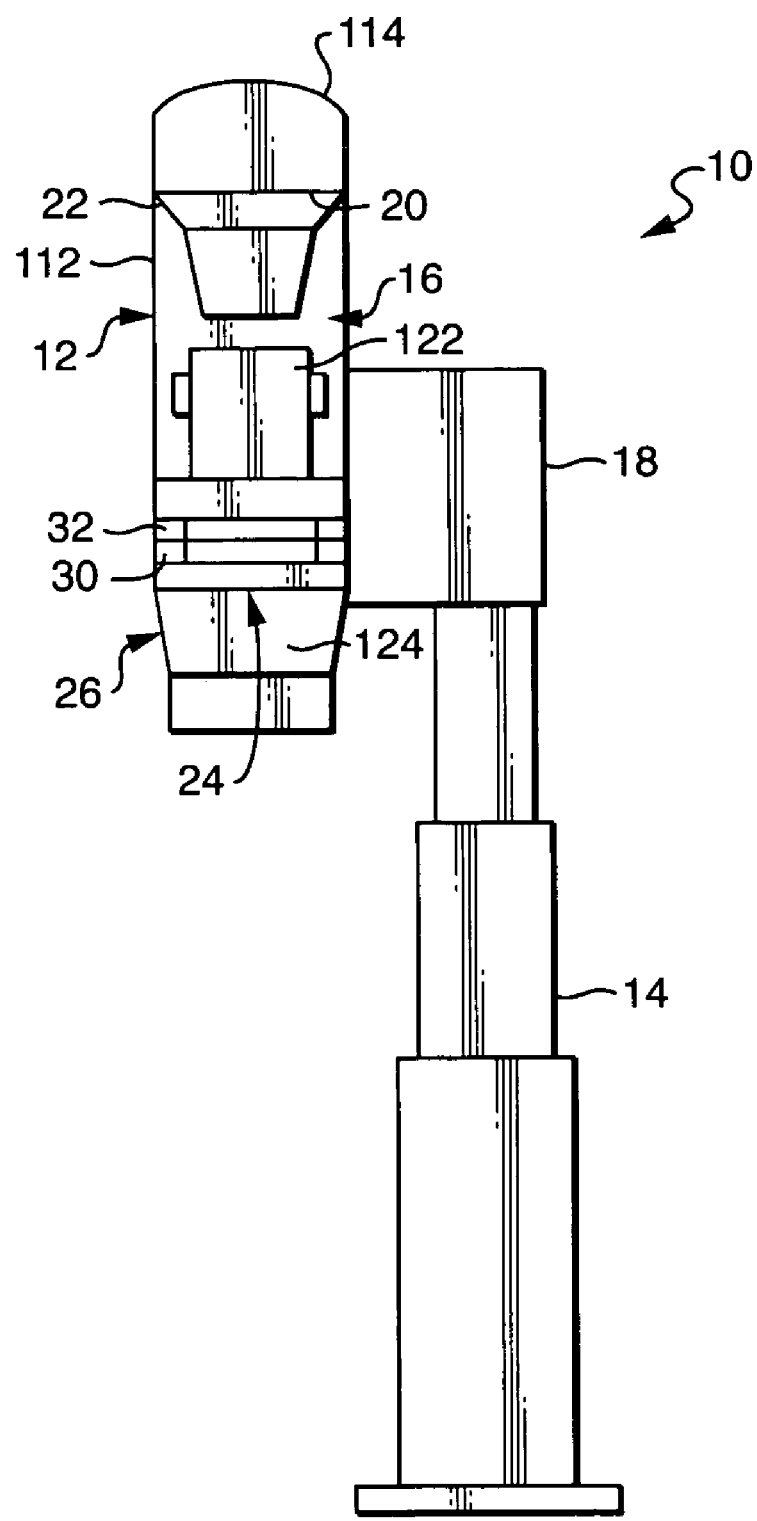
FIG. 2 is a front elevation view of the system of FIG. 1, wherein the telescoping vertical column is shown in a fully raised position.

As shown best in FIGS. 1 and 2, the support stand 14 is adjustable in height to permit the raising and lowering of the C-arm 16. In the embodiment show, for example, the support stand 14 is telescopic and can be collapsed, as shown in FIG. 1, or extended, as shown in FIG. 2. Although not shown, a motor and lifting mechanism can be provided within the stand 14 for raising and lowering the stand 14. The lifting mechanism can comprise a hydraulic piston or a rack and gear arrangement, for example. The lifting mechanism can be controlled by the same user interface component(s) (e.g., a computer keyboard or hand controller) that is used for controlling the drive assemblies 44, 46 for rotating the C-arm 16.

Figure 5:
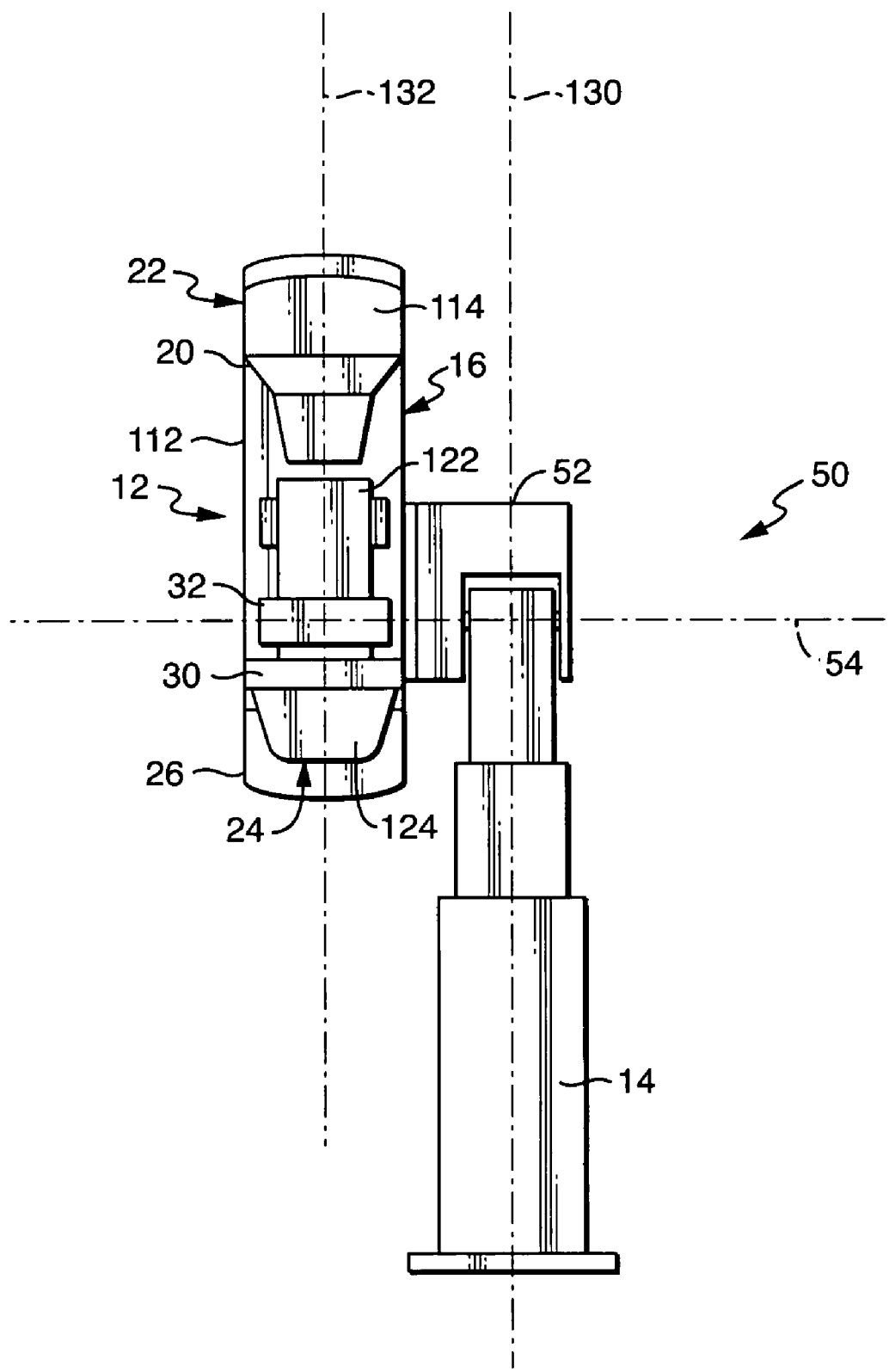
FIG. 5 is a front elevation view of another exemplary embodiment of a system constructed in accordance with the present disclosure including a mammography unit pivotally mounted on a telescoping vertical column, and wherein the column is shown in a fully raised position.
Figure 6:
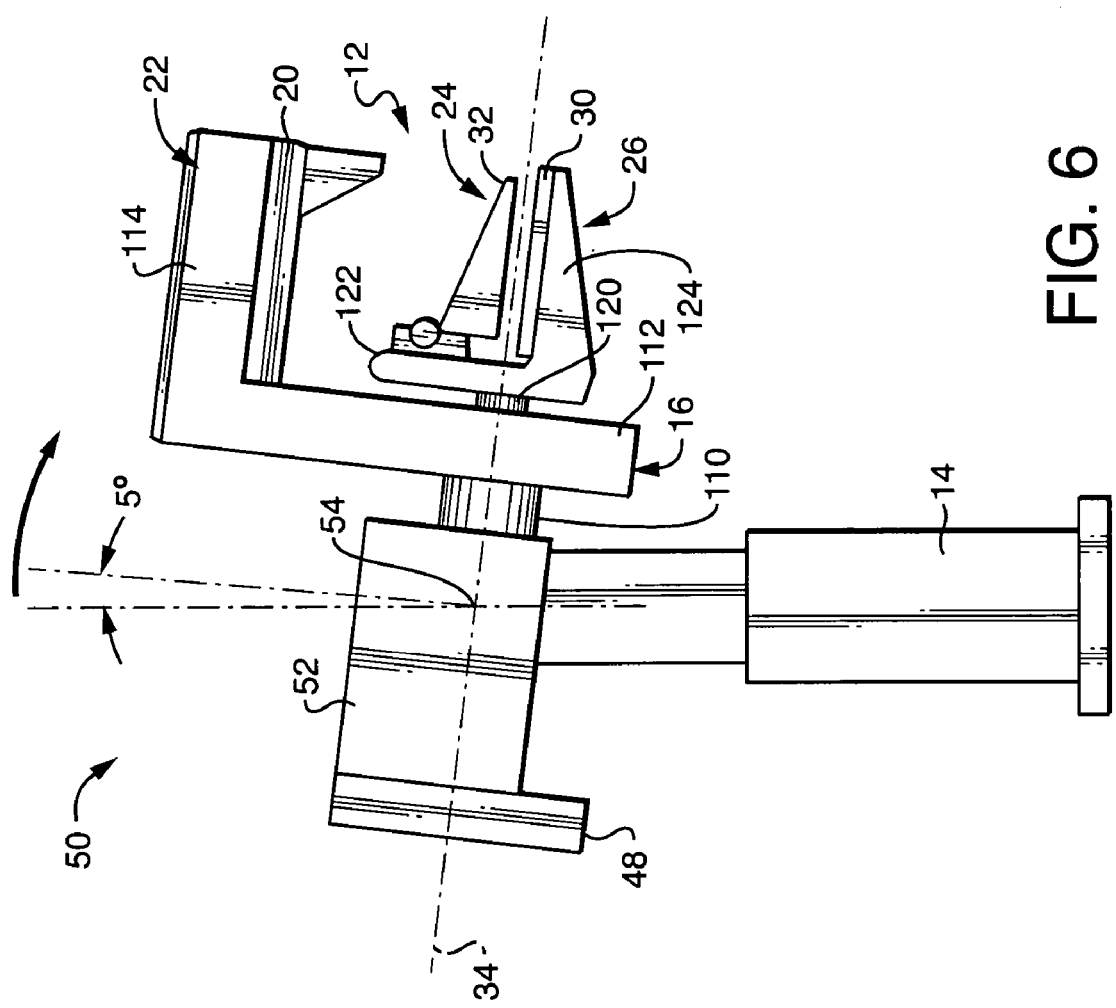
FIG. 6 is a side elevation view of the system of FIG. 5, wherein the telescoping vertical column is shown in a partially raised position and the mammography unit is shown tilted forward.
Figure 7:
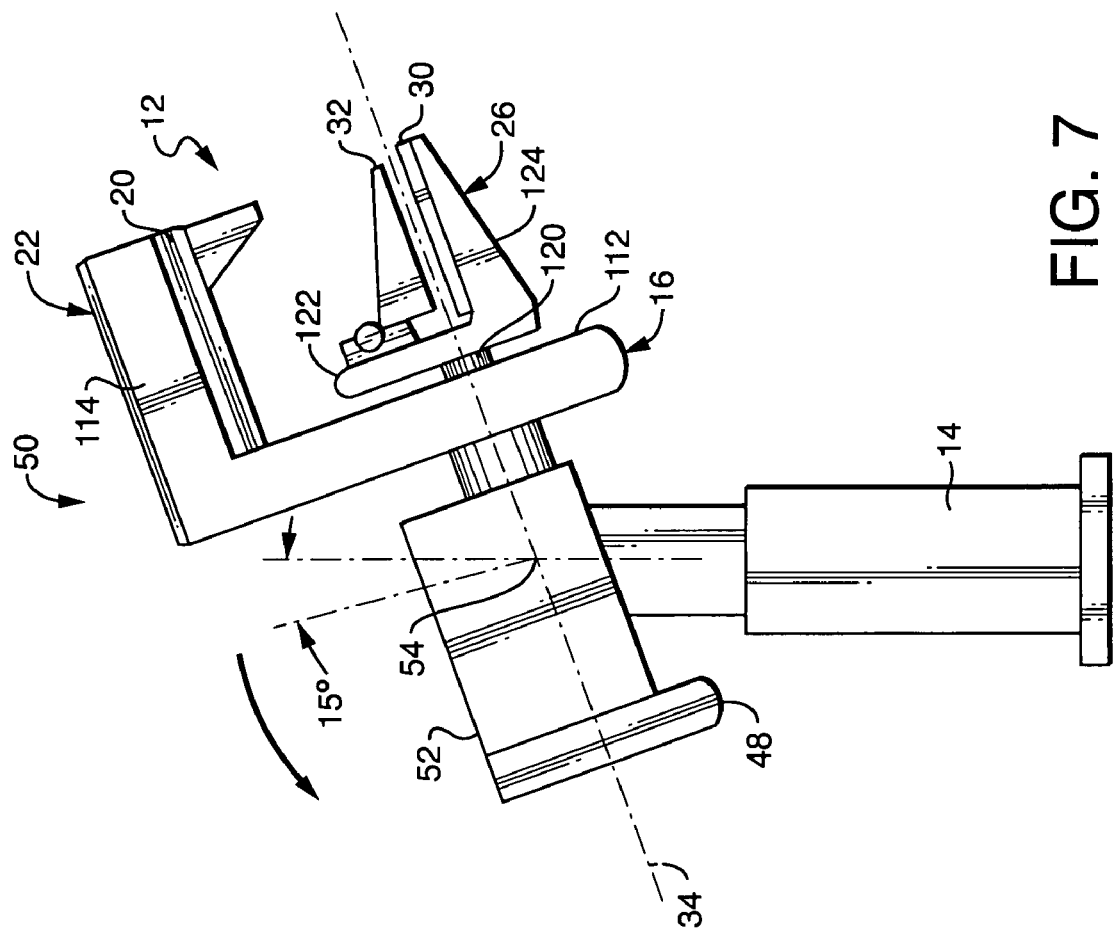
FIG. 7 is a side elevation view of the system of FIG. 5, wherein the telescoping vertical column is shown in a partially raised position and the mammography unit is shown tilted rearward.

Another exemplary embodiment of a system 50 constructed in accordance with the present disclosure is shown in FIGS. 5 through 7. The system 50 is similar to the system 10 of FIGS. 1 through 4, such that similar elements have the same reference characters. However, in the embodiment of FIGS. 5 through 7, the mammography unit 12 can be tilted back and forth on the support stand 14, in addition to being rotated.

In the exemplary embodiment of FIGS. 5 through 7, a casement 52 which supports the mammography unit 12 off to the side of the support stand 14 is pivotally mounted to the support stand 14 such that the casement 52 pivots about a tilt or pivot axis 54, which intersects the support stand 14. In particular, the C-arm 16 is mounted on the casement 52 and the casement horizontally supports the C-arm such that a vertical centerline 132 of the C-arm is horizontally offset from a vertical centerline 130 of the stand 14. Therefore, the C-arm 16 pivots about the vertical support stand 14, but never tilts toward the support stand (i.e., the tilting motion of the C-arm is not limited by the stand).

Preferably, the pivot axis 54 extends perpendicular to the rotation axis 34 of the mammography unit 12. In addition, the pivot axis 54 is substantially aligned with the rotation axis 34. The arrangement allows the C-arm 16 to be tilted forward about five degrees (5°), clockwise with reference to FIG. 6, and rearward about fifteen degrees (15°), counter-clockwise with reference to FIG. 7. Allowing the C-arm 16 to be tilted provides increased comfort to the patient, and allows more breast tissue to be examined in a manner less stressful to the patient.

In the exemplary embodiment shown, the C-arm 16 is manually tiltable and does not include a motor and tilt mechanism. However, it should be understood that the system 50 can be provided with a motor and tilt mechanism for automatically tilting the C-arm 16 about the pivot axis 54. As shown best in FIGS. 6 and 7, the coaxial drive assemblies, contained beneath the cover 48, acts as a counter weight for the C-arm 16. The counter-weight action substantially reduces the energy needed to manually tilt the C-arm 16, and adds to the overall safety of the system.

It should be understood that the embodiments of the present disclosure described herein are merely exemplary and that a person skilled in the art may make variations and modifications to the embodiments described without departing from the spirit and scope of the present disclosure. All such equivalent variations and modifications are intended to be included within the scope of these disclosure as defined by the appended claims.

What is claimed is:

1. An x-ray mammography system, comprising:
   a C-arm including a first portion having a distal segment extending in a first direction substantially parallel to a rotation axis of the C-arm, and a second portion having a distal segment extending in the first direction substantially parallel to the rotation axis, wherein both of the first and the second portions of the C-arm can be rotated independently about the rotation axis;
   an x-ray tube mounted on the distal segment of the first portion of the C-arm; and
   a compressor-Bucky assembly mounted on the distal segment ofthe second portion of the C-arm facing the x-ray tube; and
   a stand supporting a casement, wherein the first portion of the C-arm is mounted for rotation on a first set of bearings in the casement and the second portion of the C-arm is mounted for rotation on a second set of bearings in the casement, wherein the first portion of the C-arm includes a tubular base and the first set of bearings are located between the base of the first portion and the casement, and the second portion of the C-arm includes a base coaxially received within the tubular base of the first portion and the second set of bearings are located between the base of the first portion and the base of the second portion.

2. A system according to claim 1, wherein the base of the first portion and the base of the second portion are coaxially aligned with the rotation axis of the C-arm.

3. A system according to claim 1, wherein driven gears radially extend from the base of the first portion and the base of the second portion and separate drive assemblies are operatively connected to the gears.

4. A system according to claim 3, wherein the drive assemblies include motors having drive gears and pulleys operatively connecting the drive gears of the motors to the driven gears of the C-arm.

5. A system according to claim 1, wherein the compressor-Bucky assembly includes a film receptor and a plate-like compressor movable with respect to the film receptor such that a woman's breast may be positioned and compressed between the compressor and the film receptor during a mammography examination.

6. A system according to claim 1, wherein a support stand having an adjustable height supports the C-arm.

7. A system according to claim 6, wherein the support stand is telescopic and can be collapsed or raised.

8. A system according to claim 7, wherein a lifting mechanism is provided within the stand for raising and lowering the stand.

9. A system according to claim 8, wherein the lifting mechanism comprises a hydraulic piston.

10. A system according to claim 1, wherein the C-arm can be tilted back and forth about a pivot axis extending generally perpendicular to the rotation axis of the C-arm.

11. A system according to claim 10, further comprising:
a vertically extending stand;
a casement pivotally mounted to the stand so that the casement can be pivoted about the pivot axis; and
wherein the C-arm is mounted on the casement and the casement horizontally supports the C-arm such that a vertical centerline of the C-arm is horizontally offset from a vertical centerline of the stand.

12. A system according to claim 10, wherein the C-arm can be tilted about the pivot axis forward about five degrees (5°) and rearward about fifteen degrees (15°).

13. A system according to claim 10, further comprising a motor for automatically tilting the C-arm about the pivot axis.

* * * * *